US00PP20125P2

(12) United States Plant Patent
Gossett

(10) Patent No.: US PP20,125 P2
(45) Date of Patent: Jun. 23, 2009

(54) ***SEDUM* PLANT NAMED 'CLASS ACT'**

(50) Latin Name: *Sedum spp.*
Varietal Denomination: Class Act

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/148,085

(22) Filed: Apr. 15, 2008

(51) Int. Cl.
*A01H 5/00* (2006.01)

(52) U.S. Cl. ..... Plt./479
(58) Field of Classification Search ..... Plt./479
See application file for complete search history.

*Primary Examiner*—June Hwu
(74) *Attorney, Agent, or Firm*—Klarquist Sparkman, LLP

(57) ABSTRACT

A new and distinct hybrid of *Sedum* plant substantially as shown and described, with deep red purple flowers with prominent cream colored bud, green leaves edged red, and a short, stiff upright habit.

1 Drawing Sheet

Botanical denomination: *Sedum* spp.
Variety Designation: 'Class Act'.
Parentage: *S. spectabile* 'Brilliant'×*S. telephium* dark leaf.
Compared with *Sedum* 'Mr. Goodbud' (U.S. Plant Pat. No. 17671).

The present invention relates to a new and distinct cultivar of *Sedum* and given the cultivar name of 'Class Act'. *Sedum* is in the family *Crassulaceae. Sedum* 'Class Act' originated from an open pollinated cross between *Sedum spectabile,* 'Brilliant', unpatented, as the seed parent and an unknown and unpatented dark leaf *Sedum telephium* as the pollen parent.

This new and unique *Sedum* is distinguished by:

1. Large dark red purple flowers.
2. Cream colored buds.
3. Dark leaf margins.
4. Short stature.
5. Stiff, upright habit.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a 1 and a half year old *Sedum* 'Class Act' growing in the ground in the trial fields in August in Canby, Oreg.

DETAILED PLANT DESCRIPTION

The following is a detailed description of the new *Sedum* hybrid based on observations of one and a half year old specimen grown in a the ground in full sun under typical outdoor conditions in the trial fields in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Plant:
- *Type.*—Herbaceous perennial.
- *Hardiness.*—USDA Zone 4 to 9.
- *Size.*—36 cm tall from the ground to the top of the foliage and 32 cm wide.
- *Habit.*—Erect, clumping.
- *Vigor.*—Excellent.
- *Root description.*—Multiple fleshy roots from each crown, Greyed Yellow (RHS 161C), grows to 5 mm wide and 20 cm long in clay loam soil.

Stem:
- *Height.*—14 cm.
- *Width.*—19 mm.
- *Color.*—Yellow Green (RHS 147C).
- *Texture.*—Succulent.
- *Surface.*—Glaucous.

Leaf:
- *Type.*—Simple.
- *Arrangement.*—Opposite.
- *Shape.*—Elliptic to slightly obovate.
- *Apex.*—Broadly acute.
- *Base.*—Cuneate.
- *Venation.*—Pinnate.
- *Margins.*—Coarsely and irregularly serrate.
- *Blade size.*—7 cm to 14 cm long and 3 cm to 6 cm wide.
- *Surface.*—Glabrous.
- *Texture.*—Thick, spongy, succulent.
- *Petiole.*—Leaves sessile.
- *Leaf color.*—Topside Green (RHS 137B) edged with Greyed Purple (RHS 187A) Bottom side (RHS Green 138B) lightly tinged with (RHS Greyed Purple 187A).

Inflorescence:
- *Type.*—Terminal, corymbose, umbel-like.

*Number of flowers.*—Over a 1000 per stem (increases with age).

*Peduncle.*—17 cm tall and 4 mm to 6 mm wide, Greyed Green (RHS 193A) tinged with Greyed Purple (RHS 187A), succulent, glaucous.

*Branching.*—5 main branches per stem.

*Bloom period.*—August through September in Canby, Oreg.

*Inflorescence size.*—28 cm wide, 13 cm deep.

Flower Bud:

*Size.*—3 mm wide, 8 mm deep.

*Description.*—Ovoid.

*Color.*—Yellow White (RHS 158C) with narrow lines of Red Purple (RHS 59C).

Flower:

*Type.*—Complete, actinomorphic.

*Shape.*—Stellate.

*Size.*—10 mm deep and 12 mm wide.

*Color.*—Red Purple (RHS 59B) to (RHS 59C).

*Corolla description.*—5 in number, petals lanceolate, 8 mm long and 1.5 mm wide, entire, glabrous on both sides, acute, Red Purple 59C on both sides.

*Calyx description.*—Campanulate, 5 lobes, 3 mm deep and 3 mm wide, divided ⅚ to the base, entire, acute, glabrous to glaucous, Greyed Green (RHS 194A) on both sides.

*Stamen description.*—5 in number, 7.5 mm long, filaments 7 mm long, Red Purple (RHS 59C to 62D), anthers Greyed Purple (RHS 187A), no pollen, male sterile.

*Pistil description.*—5 separate prominent carpets, each 9 mm deep and 4 mm wide, Red Purple (RHS 59C to 62D).

*Fragrance.*—None.

*Lastingness.*—Each stem lasts up to a month.

Fruit:

*Type.*—Ventrally dehiscent follicle, erect, attenuate.

*Fertility.*—None.

*Color.*—Greyed Purple (RHS 187A) at top and gray tan at bottom, Grey (RHS 200B).

Seed: No seed produced.

Disease and pest resistance or tolerance: All *Sedum* species are susceptible to root rots with poor drainage. They are also susceptible to mealybug, scale, slugs and snails. None of these insect problems have been noted on the new variety.

COMPARISON TO SIMILAR *SEDUM*

Compared to *Sedum spectabile* 'Brilliant', the unpatented seed parent, *Sedum* 'Class Act' is shorter, more stiffly upright, with darker leaves and leaf margins. The leaves are held more upright on the stem and the flowers are of a duller color. Compared to *Sedum telephium,* 'Atropurpureum' and other dark leaf forms, *Sedum* 'Class Act' has greener leaves, lighter stems, and showier flowers.

Compared to *Sedum* 'Mr. Goodbud' (U.S. Plant Pat. No. 17671), the new variety has a slightly taller and narrower habit, a later bloom time, and a deeper red purple flower color.

I claim:

1. A new and distinct hybrid of *Sedum* plant as herein illustrated and described.

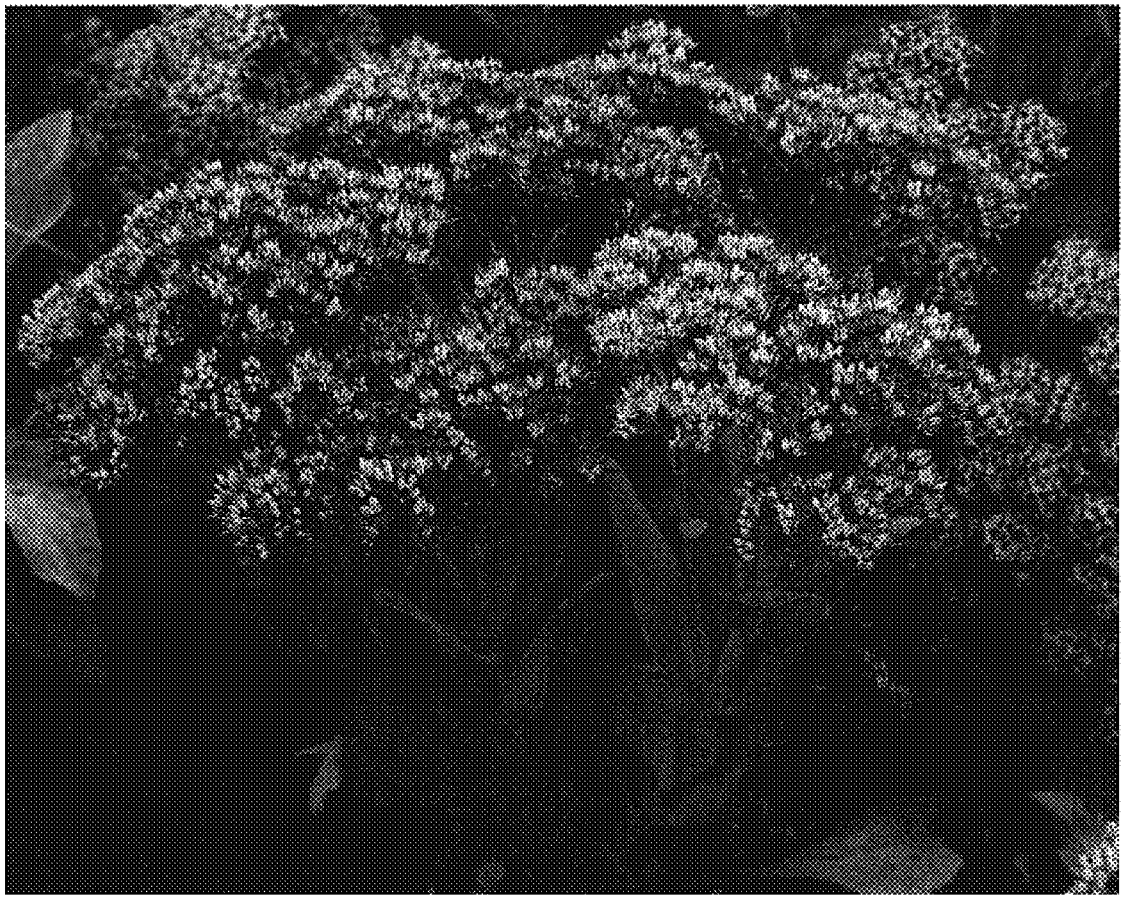

* * * * *